United States Patent [19]

Fujishiro, Takeshi

[11] 4,298,573
[45] Nov. 3, 1981

[54] DEVICE FOR DETECTION OF OXYGEN CONCENTRATION IN COMBUSTION GAS

[75] Inventor: Takeshi Fujishiro Yokosuka, Japan

[73] Assignee: Nissan Motor Company, Limited, Yokohama, Japan

[21] Appl. No.: 150,059

[22] Filed: May 15, 1980

[30] Foreign Application Priority Data

May 19, 1979 [JP] Japan .................................. 54-61023

[51] Int. Cl.³ ...................... G01N 27/46; G01N 33/22
[52] U.S. Cl. .................................... 422/94; 23/232 E; 73/26; 204/195 S; 422/98
[58] Field of Search ................. 422/94, 98; 23/232 E; 73/23, 26, 27 R; 204/1 T, 195 S

[56] References Cited

U.S. PATENT DOCUMENTS 3,597,345  8/1971  Hickam et al. ......................... 422/94
3,791,936  2/1974  Pebler et al. ....................... 422/94 X
4,063,897  12/1977 Aoki ..................................... 422/94
4,101,403  7/1978  Kita et al. ......................... 204/195 S Primary Examiner—Ronald Serwin Attorney, Agent, or Firm—Schwartz, Jeffery, Schwaab, Mack, Blumenthal & Koch

[57] ABSTRACT

A device suitable for use in engine exhaust gas to detect actual air/fuel ratio of air-fuel mixture supplied to the engine. The probe of the device has three electrodes. An oxygen ion conductive solid electrolyte occupies a space between the first and second electrodes, and a porous layer of similar solid electrolyte occupies a space between the second and third electrodes such that exhaust gas directly contacts the first and third electrodes and also contacts the second electrode through the porous solid electrolyte layer. At least one of the first and second electrodes, particularly the second, is made of a catalytic material, and the first and second electrodes serve as output terminals of the probe. Preferably the second and third electrodes are connected to a DC power supply to force a current to flow through the porous solid electrolyte layer to control oxygen partial pressure at the second electrode surface. By selectively determining catalysis of the first and second electrodes and/or the direction or intensity of the current, air/fuel ratios above, below and equal to a stoichiometric ratio can be detected.

11 Claims, 23 Drawing Figures

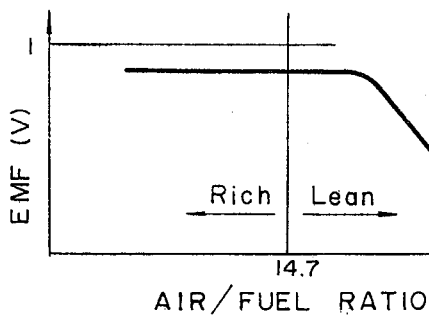
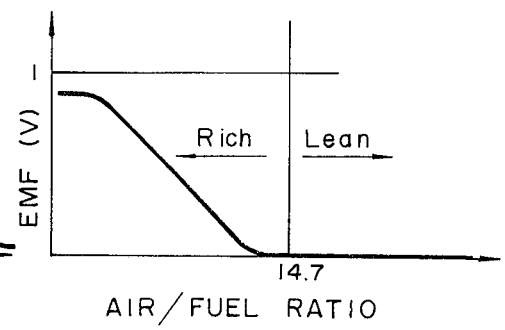
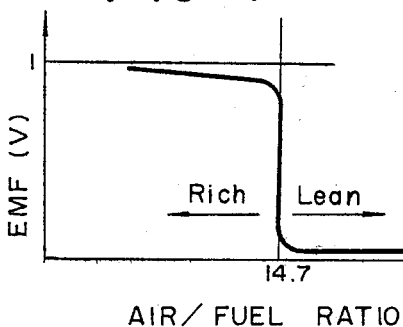
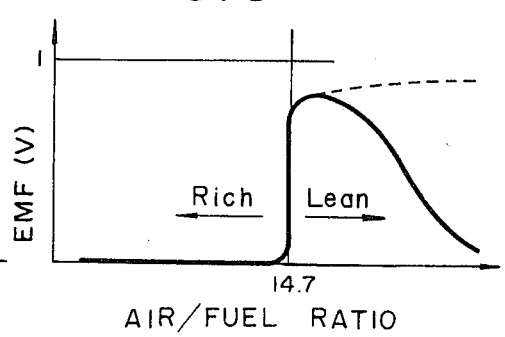
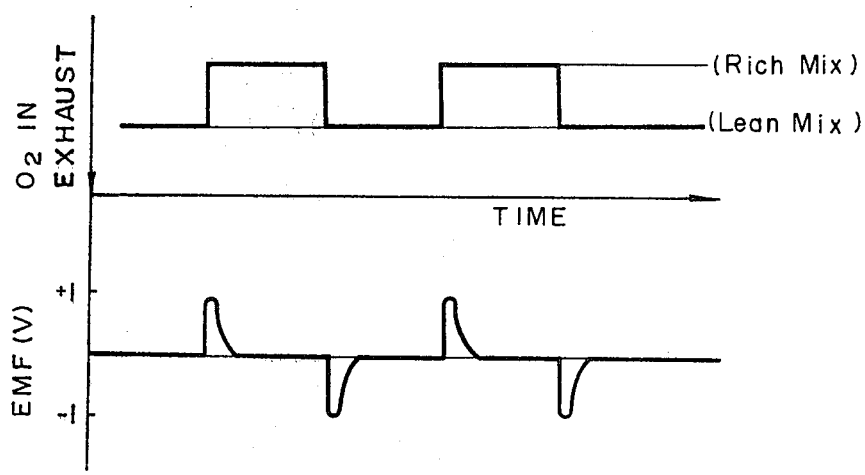

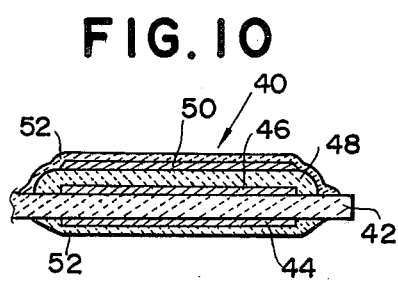
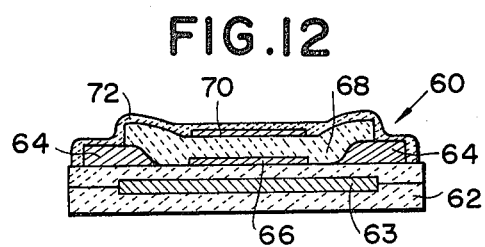
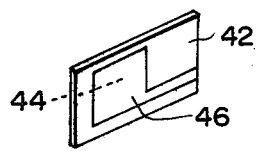
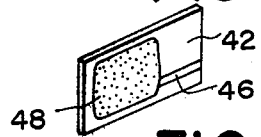
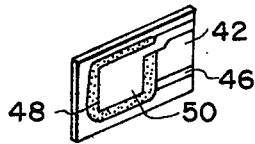
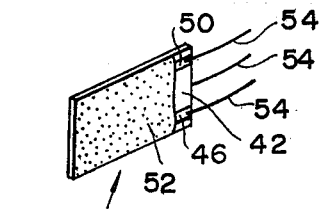
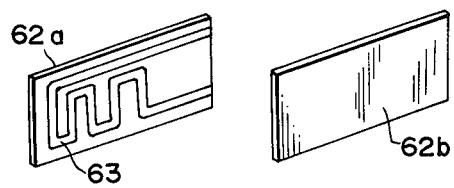
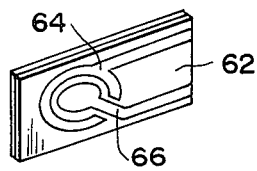
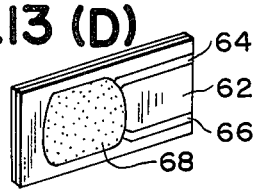
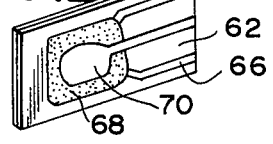
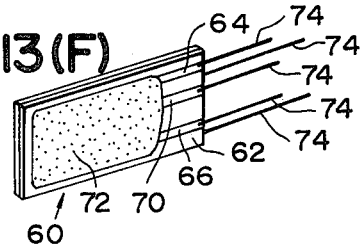

DEVICE FOR DETECTION OF OXYGEN CONCENTRATION IN COMBUSTION GAS

BACKGROUND OF THE INVENTION

This invention relates to a device for detecting the concentration of oxygen in a combustion gas, which device is of the type having at least one layer of an oxygen ion conductive solid electrolyte and is particularly suitable for use in an exhaust system of a combustion engine to detect an actual air/fuel ratio of an air-fuel mixture supplied to the engine by detecting the concentration of oxygen in the exhaust gas.

In the field of internal combustion engines, and particularly in automotive engines, it has been popularized to detect changes in the air/fuel ratio of an air-fuel mixture actually supplied to the engine as the basis for feedback control of the air/fuel ratio by detecting changes in the concentration of oxygen in the exhaust gas. This is because usually it is more convenient to provide an oxygen sensor to the exhaust system of the engine than to the intake system. Most of the oxygen sensors conventionally used for this purpose are of the concentration cell type having a layer of an oxygen ion conductive solid electrolyte, a measurement electrode layer porously formed on one side of the solid electrolyte layer and a reference layer formed on the other side. These oxygen sensors are designed and used such that the measurement electrode is exposed to the exhaust gas while the reference electrode is exposed to a reference gas having a known oxygen partial pressure, usually atmospheric air, whereby an electromotive force is generated across the two electrode layers because of a difference between the reference oxygen partial pressure in air and an equilibrium oxygen partial pressure in the exhaust gas. Since the magnitude of the equilibrium oxygen partial pressure in the exhaust gas depends on the air-fuel ratio of an air/fuel mixture from which the exhaust gas is produced, the electromotive force serves as an electrical signal representative of the air/fuel ratio. However, the potential of this electromotive force is not directly proportional to the air/fuel ratio. A great and sharp change occurs in the potential of the electromotive force on the occurrence of a change in the air/fuel ratio across a stoichiometric air/fuel ratio (where the excess air factor $\lambda$ of the air/fuel mixture becomes 1.0), that is, a change from a fuel-rich mixture to a lean mixture or in the reverse direction. Accordingly this type of oxygen sensors is suitable for use in engines operated with a stoichiometric or nearly stoichiometric air-fuel mixture. However, when the air-fuel ratio varies only on one side of the stoichiometric ratio the electromotive force generated by the sensor disposed in the exhaust gas exhibits only very little changes in its magnitude. Therefore, it is practically impossible to detect air/fuel ratios deviating from a stoichiometric air/fuel ratio by disposing an oxygen sensor of the above described type in the exhaust gas.

Meanwhile, in automotive gasoline engines the development of so-called lean-burn engines has been in progress mainly with the view of improving the thermal efficiency by the employment of a considerably lean air-fuel mixture (large in the value of the excess air factor $\lambda$), and attention has been given also to the so-called rich-burn engines which are operated with a considerably rich air-fuel mixture (small in the value of $\lambda$) and exhibit high mechanical efficiencies.

SUMMARY OF THE INVENTION

It is an object of the present invention to provide a novel device for detecting the concentration of oxygen in a combustion gas, which device is useful for the detection of an actual air/fuel ratio of an air-fuel mixture supplied to a combustion engine by detecting the concentration of oxygen in the exhaust gas not only when the air-fuel mixture is nearly stoichiometric but also when the air-fuel mixture is considerably deviated from a stoichiometric condition either to the lean side or to the rich side.

It is another object of the invention to provide a solid electrolyte device for detecting the concentration of oxygen in a combustion gas, thereby detecting an actual air/fuel ratio of an air-fuel mixture from which the combustion gas is produced, which device is more sensitive to a small magnitude of oxygen partial pressure in the combustion gas than conventional solid electrolyte type oxygen sensors and can be made to exhibit a variable output characteristic.

A device according to the invention has a probe which is to be disposed in a combustion gas and comprises a first electrode which is gas permeably porous, a second electrode spaced from the first electrode, a layer of an oxygen ion conductive solid electrolyte which occupies the space between the first and second electrodes, a third electrode which is gas permeably porous and spaced from the second electrode and a gas permeably porous layer of an oxygen ion conductive solid electrolyte which occupies the space between the second and third electrodes. The three electrodes are arranged such that the combustion gas directly contacts the first and third electrodes and also contacts the second electrode through micropores in the solid electrolyte layer interposed between the second and third electrodes. At least one of the first and second electrodes is made of a material which exhibits a catalytic action on oxidation reactions. The device is used with a meter means connected to the first and second electrodes of the probe for measuring an electromotive force generated by the solid electrolyte layer between these two electrodes.

Preferably, this device further comprises a DC power source connected to the second and third electrodes of the probe to force a current to flow through the porous layer between the second and third electrodes.

In the present invention, it is contemplated to enhance the sensitivity of the surface of the second electrode, i.e., one of the two electrodes provided to a solid electrolyte layer employed to generate an electromotive force as the output of the device, to the concentration of oxygen in a combustion gas first by the provision of a porous solid electrolyte layer on this electrode to control the diffusion of gas component molecules to the electrode surface thereby to control the magnitude of oxygen partial pressure at the surface of this electrode. The control of the magnitude of oxygen partial pressure at this electrode surface can be made more effective by forcing a DC current to flow through this porous solid electrolyte layer thereby causing oxygen ions to migrate through this solid electrolyte layer.

As the result, in a combustion gas, this device can be made to exhibit a significant change in the magnitude of electromotive force measured between the first and second electrodes not only when the air/fuel ratio of an air-fuel mixture from which the combustion gas is produced changes across a stoichiometric ratio but also when the air/fuel ratio varies only on one side of the stoichiometric ratio. Accordingly this device is applicable to either lean-burn engines or rich-burn engines as well as engines operated with a nearly stoichiometric air-fuel mixture.

BRIEF DESCRIPTION OF THE DRAWINGS

FIGS. 3-6 are graphs showing output characteristics respectively exhibited by several kinds of embodiments of the present invention disposed in an engine exhaust gas resulting from combustion of an air-fuel mixture of which the air/fuel ratio is varied over a wide range;

FIG. 7 is a chart showing an output characteristic exhibited by an embodiment of the present invention disposed in an engine exhaust gas resulting from combustion of an air-fuel mixture of which the air/fuel ratio exhibits a periodic change;

FIG. 10 is a cross-sectional view of an essential part of a practical oxygen concentration detection device as an embodiment of the invention;

FIGS. 11(A) to 11(D) illustrate a process of fabricating the device of FIG. 10;

FIG. 12 is a cross-sectional view of an essential part of a practical oxygen concentration detection device as another embodiment of the invention;

FIGS. 13(A) to 13(F) illustrate a process of fabricating the device of FIG. 12;

DESCRIPTION OF THE PREFERRED EMBODIMENTS

Figure 1:
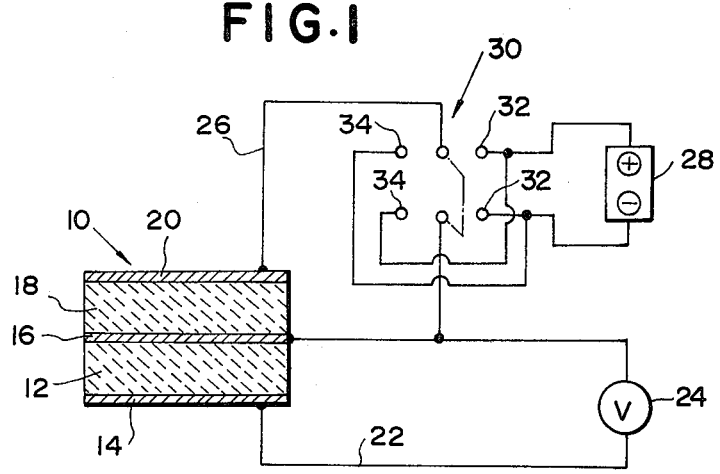
FIG. 1 shows schematically and sectionally a fundamental construction of an oxygen concentration measurement device according to the invention.

FIG. 1 is a schematic illustration of an embodiment of the present invention for the purpose of explaining the principle of the function and features of a device according to the invention. An oxygen sensing element or probe 10 of this device has a layer 12 of an oxygen ion conductive solid electrolyte, a first electrode layer 14 formed on one side of the solid electrolyte layer 12 and a second electrode layer 16 formed on the other side of the electrolyte layer 12, another layer 18 of an oxygen ion conductive solid electrolyte located on the second electrode layer 16 so as to sandwich this electrode layer 16 between the two solid electrolyte layers 12 and 18 and a third electrode layer 20 formed on the outside of the solid electrolyte layer 18. Thus, this probe 10 has three electrode layers 14, 16 and 20 arranged such that the second electrode 16, i.e., one located in the interior of the probe 10, is separated from the first electrode layer 14, which is formed on the outside of the probe 10, by a solid electrolyte layer and from the third electrode layer 20, which too is formed on the outside of the probe 10, also by a solid electrolyte layer. Each of these electrode layers 14, 16 and 20 is made of an electronically conductive material and has a microscopically porous or gas permeable structure. The solid electrolyte layer 18 too has a microscopically porous or gas permeable structure. The solid electrolyte layer 12 sandwiched between the first and second electrode layers 14, 16 is made to have a dense and gas impermeable structure, but, when a device according to the invention includes a DC power source connected to the second and third electrode layers 16 and 20 as described hereinafter, it is permissible that this solid electrolyte layer 12 too has a microscopically porous structure. Thus, the first and third electrode layers 14 and 20 can be exposed directly to a gas subject to measurement, but the gas contacts the second electrode layer 16 only through the porous solid electrolyte layer 18 (when the other solid electrolyte layer 12 has a gas impermeable structure). In this probe 10, at least one of the two solid electrolyte layers 12, 18 is so designed as to serve as a structurally basic member of the probe 10.

The first and second electrode layers 14 and 16 are connected by leads 22 to a potentiometer 24 or an equivalent means for measuring an electromotive force generated across the solid electrolyte layer 12 during operation of this probe 10. Besides, the second and third electrode layers 16 and 20 are connected by leads 26 to a DC power source 28 via a double-pole double-throw switch 30 which is employed to selectively switch over the polarity of a DC voltage applied to these two electrode layers 16, 20.

For the solid electrolyte layers 12 and 18, any one of the oxygen ion conductive solid electrolytes used in conventional oxygen sensors can be employed. Some examples are $ZrO_2$ stabilized with CaO, $Y_2O_3$ or MgO, $ThO_2$-$Y_2O_3$ system and CaO-$Y_2O_3$ system.

As mentioned hereinbefore, it is a feature of the invention that the output characteristic of the illustrated probe 10 in an engine exhaust gas can be varied by selection of materials for the first and second electrode layers 14, 16 and also by the manner of applying a DC voltage to the second and third electrode layers 16 and 20. Useful materials for the first and second electrode layers 14 and 16 are classified into two categories, that is, a group of conductive materials which exhibit catalytic action on oxidation reactions as typified by Pt, other metals of the platinum group including alloys thereof and alloys of a platinum group metal with a base metal; and a group of noncatalytic conductive materials exemplified by Au, Ag, SiC, $SnO_2$ which may be mixed with $V_2O_5$, PbO and/or $Al_2O_3$, and ceramic-like materials having a Perovskite structure such as ones obtained by adding Ca, Zr, Mg or Sr to $LaCrO_3$, $LaNiO_3$ or $SmCoO_3$. The third electrode layer 20 may be made of any type of electrode material, that is, either a catalytic material or a noncatalytic material, irrespective of the materials employed for the first and second electrode layers 14 and 16.

According to the type of materials for the first and second electrode layers 14 and 16 and the manner of supplying a DC current to the solid electrolyte layer 18 sandwiched between the second and third electrode layers 16, 20, a device according to the invention can be produced in seven different types as shown in the following Table. When used in an exhaust gas stream discharged from a gasoline engine, these seven different types of devices are different in their output characteristic, that is, the relationship between actual air/fuel ratio of an air-gasoline mixture supplied to the engine and an electromotive force generated across the solid electrode layer 12 in FIG. 1, as explanatorily shown in FIGS. 3-9.

Figure 8:
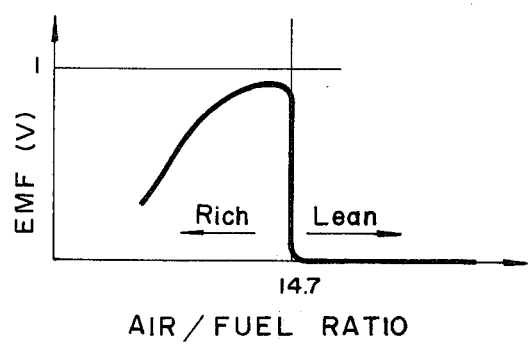
FIGS. 8 and 9 are graphs showing two types of output characteristics exhibited by another embodiment of the present invention disposed in an engine exhaust gas as mentioned with respect to FIGS. 3-6.
Figure 9:
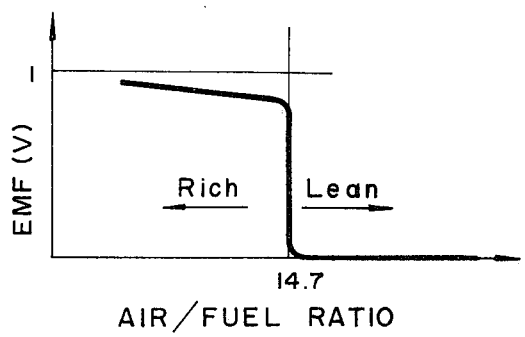

| Type of Device | Catalytic Activity of Electrode Layers | | | Connection of Electrodes to DC Power Source | | Current Intensity | Air/Fuel Ratio vs EMF |
|---|---|---|---|---|---|---|---|
| | 1st | 2nd | 3rd | 2nd | 3rd | | |
| A-1 | no | yes | yes or no | negative | positive | adequate | FIG. 3 |
| A-2 | no | yes | yes or no | not connected | | zero | FIG. 4 |
| A-3 | no | yes | yes or no | positive | negative | adequate | FIG. 5 |
| B | yes | no | yes or no | not connected | | zero | FIG. 4 |
| C-1 | yes | yes | yes or no | negative | positive | adequate | FIG. 6 |
| C-2 | yes | yes | yes or no | not connected | | zero | FIG. 7 |
| C-3 | yes | yes | yes or no | positive | negative | adequate | FIG. 8 |
| C-3 | yes | yes | yes or no | positive | negative | high | FIG. 9 |

The function of the respective types of devices will be described in the same order as in the Table.

Type A-1

In this case the first electrode layer 14 in FIG. 1 exhibits a catalytic activity on oxidation reactions of HC (hydrocarbons), CO, etc. contained in the exhaust gas, but the other of the outer electrode layers, i.e. third electrode layer 20, does not exhibit such a catalytic activity. The DC power source 28 is connected to the probe 10 by utilizing contacts 32 of the switch 30, so that the third electrode layer 20 is connected to the positive terminal of the DC power source 28 and the second electrode layer 16 to the negative terminal, thereby keeping a DC current of a predetermined intensity flowing between the third and second electrode layers 16 and 20 through the porous solid electrolyte layer 18 during operation of the device.

When the probe 10 of this type is disposed in an exhaust gas stream of a gasoline engine, the magnitude of an oxygen partial pressure at the outer surface of the first electrode layer 14, and hence at the interface between this electrode layer 14 and the solid electrolyte layer 12, remains on the level of $10^{-2}$ to $10^{-3}$ atm whether the engine is fed with a considerably rich mixture or fed with a considerably lean mixture because of the noncatalytic property of this electrode layer 14. When the engine is operated with a rich mixture, the magnitude of an oxygen partial pressure at the upper (in FIG. 1) surface of the second electrode layer 16, and hence at the interface between this electrode layer 16 and the solid electrolyte layer 12, lowers to the level of $10^{-15}$ to $10^{-30}$ atm because a very small quantity of oxygen molecules contained in the exhaust gas produced by combustion of the rich mixture are almost entirely consumed by oxidation reactions at the outer surface of the third electrode layer 20. In this state, an electromotive force of a relatively high potential as shown in the left side of FIG. 3 is generated by the solid electrolyte layer 12 of this probe 10.

Figure 2:
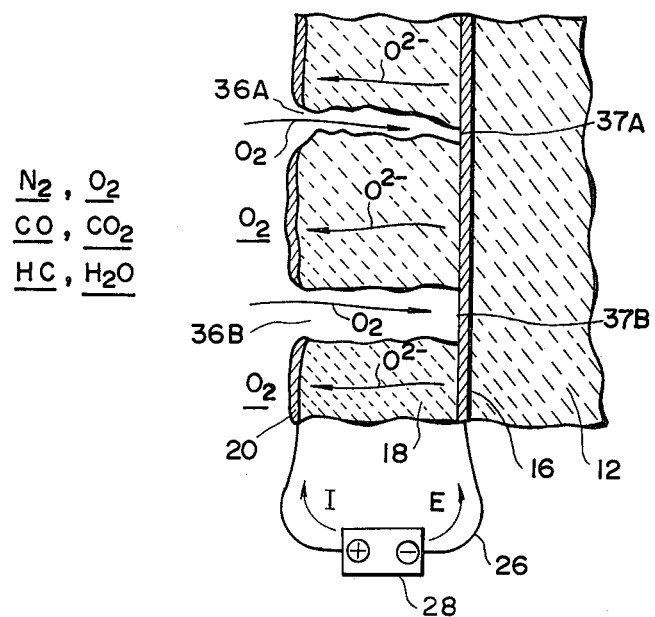
FIG. 2 is a schematically enlarged illustration of a microscopically small portion of the device of FIG. 1 for explanation of the principle of the function of this device.

Next, the function of the same device (type A-1) in the case of operating the engine with a lean mixture will be explained with reference to FIG. 2 too. Since a DC current (in FIG. 2 indicated by the arrow I, while the arrow E indicates the movement of electrons) is forced to flow between the third and second electrode layers 20 and 16, oxygen ions migrate through the solid electrolyte layer 18 from the second electrode layer 16 towards the third electrode layer 20 and, at the same time, oxygen molecules diffuse from the exhaust gas into micropores (in FIG. 2 represented by through holes 36A, 36B) in the porous solid electrolyte layer 18. The hole 36A is representative of micropores or interstices relatively small in width and/or relatively long in effective length or diffusion distance. At the inner terminal 37A of the hole 36A, there occurs shortage of oxygen because of slowness of diffusion of oxygen molecules in this hole 36A. The hole 36B represents micropores or interstices relatively large in width and/or relatively short in diffusion distance, so that oxygen molecules easily diffuse through this hole 36B. Therefore, the magnitude of oxygen partial pressure at the inner terminal 37B of this hole 36B becomes nearly equal to the oxygen partial pressure in the exterior exhaust gas and remains on the level of $10^{-2}$ to $10^{-3}$ atm. In contrast, the oxygen partial pressure at 37A will become $10^{-15}$ to $10^{-30}$ atm by reason of consumption of oxygen in oxidation reactions of CO and HC and insufficiency of oxygen supply through the hole 36A.

There are innumerable micropores, both those represented by the hole 36A and those represented by the hole 36B, and for some of these micropores the oxygen partial pressure at their inner terminal becomes as explained with respect to 37A in FIG. 1, while oxygen partial pressure at the inner terminal of the remaining micropores becomes as explained with respect to 37B. The proportion of the pore terminals in the state of 37A to the pore terminals in the state of 37B varies depending on the oxygen partial pressure in the exterior exhaust gas: the pore terminals in the state of 37A increase as the air/fuel ratio of the lean mixture nears the stoichiometric ratio (14.7 for an air-gasoline mixture), but the pore terminals in the state of 37B increase as the air/fuel ratio becomes higher. Thus, an oxygen partial pressure as a balance between the flow of oxygen ions through the solid electrolyte layer 18 and the gas diffusion in the micropores represented by the holes 36A and 36B is established at the interface between the second electrode layer 16 and the solid electrolyte layer 12. This oxygen partial pressure is below the oxygen partial pressure in the exhaust gas while the air/fuel ratio is higher than but not greatly deviated from the stoichiometric ratio and, as the air/fuel ratio is raised further, gradually rises towards the oxygen partial pressure in the exhaust gas. Therefore, the magnitude of EMF generated by the solid electrolyte layer 12 varies with respect to the air/fuel ratio in the manner as shown on the right side of FIG. 3. As can be seen in FIG. 3, in this case the probe 10 does not exhibit a sharp and abrupt change in the magnitude of EMF it generates because of a considerable distribution of the dimensions of the micropores such as width and effective length. That is, there is a great dispersion in oxygen partial pressure at the surface of the second electrode layer 16 when this layer 16 is examined in microscopically small areas, so that the EMF generated by the solid electrolyte layer 12 is actually a mixed potential. Therefore, it is possible to control the EMF-generating characteristic of the probe 10 by regulating the width, effective length, etc. of the micropores in the solid electrolyte layer 18.

As will be understood from the foregoing explanation, it is possible to detect air/fuel ratio values of a lean mixture supplied to an engine by operating the type A-1 device in the exhaust gas.

Type A-2

The type A-2 device is similar to the type A-1 device in the construction of the probe 10, but in this case the switch 30 in FIG. 1 is kept in the neutral position so that the second and third electrode layers 16 and 20 are not connected to the DC power sourc 28. Because of the catalytic activity of the second electrode layer 16 and noncatalytic property of the first electrode layer 14, the probe 10 of the A-2 type device in the engine exhaust gas generates a relatively large magnitude of EMF when the engine is fed with a rich mixture, but when a lean mixture is used the magnitude of the EMF becomes nearly zero. As shown in FIG. 4, there occurs a great and sharp change in the magnitude of EMF generated by the A-2 type device when actual air/fuel ratio of the mixture supplied to the engine changes across the stoichiometric ratio.

Type A-3

The type A-3 device too is similar to the type A-1 device in the construction of the probe 10. As a sole difference, the second electrode layer 16 is connected to the positive terminal of the DC power source 28 and the third electrode layer 20 to the negative terminal by utilizing contacts 34 of the switch 30. When the engine is fed with a lean mixture and the probe 10 of this device is disposed in the exhaust gas with continued application of a DC voltage to the second and third electrode layers 16, 20, the solid electrolyte layer 12 does not generate an appreciable EMF because oxygen partial pressures at the surfaces of the first and second electrode layers 14 and 16 in this state are similarly on the level of $10^{-2}$ to $10^{-3}$ atm. Even when a rich mixture of which the air/fuel ratio is close to the stoichiometric ratio is supplied to the engine, no EMF or only a very small magnitude of EMF is generated across the solid electrolyte layer 12, as shown in FIG. 5, because the magnitude of oxygen partial pressure at the second electrode layer 16 does not appreciably change from the level of $10^{-2}$ to $10^{-3}$ atm by reason of migration of oxygen ions through the solid electrolyte 18 from the third electrode layer towards the second electrode layer 16. As the air/fuel ratio of the rich mixture is further lowered, the effect of gas diffusion through micropores in the solid electrolyte layer 18, including the movement of oxygen molecules from the second electrode layer 16 towards the external exhaust gas, becomes so significant that the magnitude of oxygen partial pressure at the second electrode layer 16 gradually increases towards an ultimate value of about $10^{-20}$ atm, where the magnitude of EMF generated across the solid electrolyte layer 12 reaches about 1 V.

Accordingly it is possible to detect air/fuel ratio values of a rich mixture by the use of the A-3 type device. Moreover, a single device as illustrated in FIG. 1 can be used to detect air/fuel ratios of a lean mixture, air/fuel ratios of a rich mixture and air/fuel ratio changes across a stoichiometric ratio by selectively changing the state of the switch 30.

Type B

The probe 10 of the type B device is not connected to the DC power source 28. This device differs from the type A-2 device only in that the first and second electrode layers 14 and 16 are made respectively catalytic and noncatalytic in the reverse way to the corrresponding electrode layers in the type A-2 device. Therefore, the type B device exhibits the same output characteristic (as shown in FIG. 4) as the type A-2 device does.

Type C-1

In the type C-1 device, the first and second electrode layers 14 and 16 are both made of a catalytic material, and the second and third electrode layers 16 and 20 are connected to the DC power source 28 via the contacts 32 of the switch 30, that is, the third electrode layer 20 is connected to the positive terminal of the DC power source 28 and the second electrode layer to the negative terminal.

When the type C-1 device is used in an engine exhaust gas, the relationship between actual air/fuel ratio of an air-fuel mixture supplied to the engine and the magnitude of EMF generated by the probe 10 of this device becomes as shown in FIG. 6. When a rich mixture is supplied to the engine, the solid electrolyte layer 12 does not generate an appreciable EMF since the first and second electrode layers 14 and 16 are similarly catalytic. When the rich mixture is varied to a lean mixture there occurs a great change in the magnitude of equilibrium oxygen partial pressure at the surface of the first electrode layer 14, and at the same time the influence of the movement of oxygen through the solid electrolyte layer 18 as explained with respect to the use of the type A-1 device for a rich mixture becomes significant. Therefore, the EMF exhibits a great and sharp increase or decrease on the occurrence of a change in the air/fuel ratio across the stoichiometric ratio and a gradual change when the air/fuel ratio remains above the stoichiometric ratio and varies. This means that the type C-1 device is useful for the detection of a stoichiometric air/fuel ratio and air/fuel ratio values of a lean mixture. If the intensity of the DC current forced to flow through the solid electrolyte layer 18 is greatly increased, the dependence of the EMF generated by this device on the air/fuel ratio of a lean mixture becomes as represented by the broken line curve in FIG. 6 because of a significant increase in the quantity of oxygen ions migrating through the solid electrolyte layer 18 from the second electrode layer 16 towards the third electrode layer 20.

Type C-2

The type C-2 device has the same probe 10 as the type C-1 device, but the second and third electrode layers 16, 20 of the type C-2 device are not connected to the DC power source 28, meaning that the switch 30 in FIG. 1 is kept in the neutral position.

Although the first and second electrode layers 14 and 16 of this device are of the same property, the existence of the porous solid electrolyte layer 18 offers a physical resistance to the arrival of the exhaust gas at the surface of the second electrode layer 16. Therefore, when a rich mixture and a lean mixture are alternately fed to the engine to result in the occurrence of periodic changes in the magnitude of equilibrium oxygen partial pressure in the exhaust gas as illustrated on the upper side of the chart of FIG. 7, each time of change in oxygen partial pressure at the surface of the second electrode layer 16 of the type C-2 device disposed in the exhaust gas occurs with a time delay from the change at the surface of the first electrode layer 14, and, as a consequence, periodically the probe 10 generates a pulse-like output voltage at each occurrence of a change from a rich mixture to a lean mixture, or in the reverse way, as shown on the lower side of the chart of FIG. 7.

Thus, the type C-2 device enables to surely detect transitions between rich and lean conditions of an air-fuel mixture supplied to the engine.

Type C-3

The type C-3 device is similar to the type C-1 device in the construction of the probe 10, but in the type C-3 device the second electrode layer 16 is connected to the positive terminal of the DC power source 28 and the third electrode layer 20 to the negative terminal, for example, by utilizing the contacts 34 of the switch 30 in FIG. 1.

Therefore, the output characteristic of the type C-3 device in exhaust gases produced by combustion of rich and lean mixtures is generally reverse to that of the type C-1 device, as shown in FIG. 8. In the exhaust gas produced from a rich mixture the magnitude of EMF generated by this device becomes maximal when the air/fuel ratio is close to the stoichiometric ratio and gradually decreases as the air/fuel ratio lowers because of the catalytic property of the first and second electrode layers 14, 16 and the movement of oxygen through micropores in the solid electrolyte layer 18 caused by the DC current flowing through this layer 18. In the exhaust gas produced from a lean mixture this device does not generate an appreciable EMF, so that a great and sharp change is exhibited in the magnitude of EMF at the stoichiometric air/fuel ratio. Accordingly it is possible to detect a stoichiometric air/fuel ratio and air/fuel ratios of a rich mixture by the use of the type C-3 device.

When the intensity of the DC current forced to flow through the solid electrolyte layer 18 of the type C-3 device is made considerably great, the relationship between the air/fuel ratio of a rich mixture and the magnitude of EMF generated by this device in the exhaust gas becomes as shown in FIG. 9 because of a significant increase in the quantity of oxygen ions which migrate through the solid electrolyte layer from the third electrode layer 20 towards the second electrode layer 16.

Thus, it is possible to detect air/fuel ratios of a rich mixture, air/fuel ratios of a lean mixture and air/fuel ratio changes across a stoichiometric ratio by the use of a single device as illustrated in FIG. 1 by selectively changing the state of the switch 30 and, when desirable, varying the intensity of a DC current forced to flow between the second and third electrodes 16, 20 of the device.

As can be understood from the description with reference to FIG. 2, it is preferable to employ a constant current DC power source as the DC power source 30 in FIG. 1 from the viewpoint of realizing a stable flow of oxygen ions through the solid electrolyte layer 18 between the second and third electrode layers 16 and 20.

The probe part (e.g. probe 10 of FIG. 1) of a device according to the invention may be fabricated by designing a solid electrolyte layer interposed between the first and second electrodes, or between the second and third electrodes, so as to serve also as a structurally basic member of the probe. Alternatively, the probe part may comprise a base plate or substrate as a structually basic member. In this case, the three electrodes and the solid electrolyte layers interposed between the first and second electrodes and between the second and third electrodes are all formed on the substrate to constitute a suitably laminated structure, and it becomes possible to fabricate each of the electrodes and solid electrolyte layers in the form of a very thin layer or film. The substrate is usually made of a non-conducting and electrochemically inactive material. Furthermore, it is preferable to embed an electrical resistance heating element in the substrate in order to heat the probe during its use as a compensation means for the lowness of oxygen ion conductivity of a solid electrolyte at relatively low temperatures (in general at temperatures below about 400° C.).

Prior to the present application, it has been proposed (by co-workers at applicant's assignee) to detect air/fuel ratio values of an air-fuel mixture supplied to a combustion engine by means of a solid electrolyte device disposed in the exhaust gas and connected to a DC power source such that a current is forced to flow through a solid electrolyte layer of the device. As a fundamental difference of this proposal from the present invention, the device of this proposal has only one layer of solid electrolyte coated with two porous electrode layers which are connected both to a DC power source and to an EMF-measuring device. That is, in this device an output voltage is provided by the solid electrolyte layer through which the DC current is forced to flow. Because of such construction, the accuracy of the air/fuel ratio detection by the proposed method is adversely influenced by the inevitable dependence of the electrical resistance of a solid electrolyte on temperature. When, for example, the temperature of the solid electrolyte device lowers, the electrical resistance of the solid electrolyte increases with the result that a voltage given by the product of this resistance by the current flowing through the solid electrolyte increases. Since this voltage is added to an EMF generated by the solid electrolyte, the output voltage of the device increases as the temperature lowers irrespective of the value of the air/fuel ratio.

In the present invention, a DC current is made to flow between the second and third electrodes 16 and 20, while an EMF generated between the first and second electrodes 14 and 16 is measured as the output of the device. Therefore, the current exerts no influence on the output voltage even when the electrical resistance of the solid electrolyte layers changes by the influence of temperature.

The invention will further be illustrated by the following embodiments in practical form.

FIG. 10 shows a cross section of an oxygen-sensitive probe 40 according to the invention. This probe 40 has a densely sintered plate 42 of a $ZrO_2$-$Y_2O_3$ system, which corresponds to the solid electrolyte layer 12 in the probe 10 of FIG. 1 and serves also as a structurally basic member or substrate of this probe 40. A thin and microscopically porous first electrode layer 44 of platinum is formed on one side of the solid electrolyte plate 42, and a second electrode layer 46 of the same form and material is formed on the other side of the plate 42. The second electrode layer 46 is substantially entirely covered with a microscopically porous layer 48 of a solid electrolyte ($ZrO_2$-$Y_2O_3$), and a thin and microscopically porous third electrode layer 50 of platinum is formed on the outer surface of the solid electrolyte layer 48. Therefore, this probe 40 gives the hereinbefore described type C-1, C-2 or C-3 device. The outer surfaces of the first and third electrode layers 44 and 50 are each covered with a porous protective layer 52 of a ceramic material.

Referring to FIGS. 11(A) to 11(D), this probe 40 was produced by the following process. First, a platinum paste (dispersion of fine powder of platinum in an organic medium) was printed onto both sides of the solid electrolyte plate 42 by a thick-film-forming technique to provide the first and second electrolyte layers 44 and 46 each in a pattern as shown in FIG. 11(A). After drying of the printed platinum paste, a solid electrolyte paste prepared by dispersing finely powdered $ZrO_2$-$Y_2O_3$ system in an organic medium was printed on the outer surface of the second electrode layer 46 (still in an unfinished state) by a thick-film-forming technique to form the porous solid electrolyte layer 48 as shown in FIG. 11(B). After drying of the printed solid electrolyte paste (48), the paste-applied plate 42 in the state of FIG. 11(B) was fired in air at about 1300° C. Next, as shown in FIG. 11(C), the third electrode layer 50 was formed by depositing platinum on the outer surface of the porous solid electrolyte layer 48 by sputtering. Thereafter, as shown in FIG. 11(D), the porous protective layers 52 were formed by plasma spraying of a ceramic material so as to cover both sides of the semi-finished probe almost entirely, and platinum leads 54 were attached to the first, second and third electrode layers 44, 46 and 50 by a solderless bonding technique.

FIG. 12 shows a cross section of a differently designed oxygen-sensitive probe 60 according to the invention, which is constructed on an alumina substrate 62 and can be fabricated by a process illustrated in FIGS. 13(A) to 13(F).

Referring to FIGS. 13(A) and 13(B), two rectangularly shaped sheets 62a and 62b of green (unfired) alumina composition (comprising a binder) were used to prepare the alumina substrate 62. A platinum paste was printed onto one (62a) of these sheets to provide an electrical resistance heating element 63 in a pattern as shown in FIG. 13(A), and then the two sheets 62a and 62b were pressed against each other to unite into a single sheet (62) with the heater element 63 sandwiched therebetween. Then, as shown in FIG. 13(C), a paste containing a metal oxide powder which is electronically conductive and exhibits no catalytic action on oxidation reactions of CO and HC was printed onto one side of the yet unfired alumina substrate 62 to provide a first electrode 64 in a pattern as illustrated, and a platinum paste was printed on the same side of the substrate 62 to provide a second electrode 66 so as to leave a nearly annular space between the two electrodes 64 and 66. Next, a solid electrolyte paste indicated at 68 in FIG. 13(D) was printed on the same side of the substrate 62 so as to cover the first and second electrode layers 64, 66 (unfired state) as shown in FIG. 13(D). After drying, the paste-applied alumina sheet 62 in the state of FIG. 13(D) was fired in air at about 1300° C. to accomplish sintering of the alumina substrate 62 and simultaneously complete forming of a porous solid electrolyte layer 68 and first and second electrodes 64, 66. The aforementioned nearly annular space between the two electrodes 64 and 66 was completely filled with the solid electrolyte 68. Then, as shown in FIG. 13(E), a third electrode 70 was formed on the outer surface of the solid electrolyte layer 58 by the deposition of platinum by sputtering. The probe 60 was finished by forming a porous protective layer 72 of $ZrO_2$-CaO system by plasma spraying and attaching platinum leads 74 to the first, second and third electrodes 64, 66, 70 and the heater element 63.

This probe 60 gives the hereinbefore described type A-1, A-2 or A-3 device.

It is a feature of the present invention to control the diffusion of gas and flow of oxygen ions in a porous solid electrolyte layer by keeping a current of an adequate intensity flowing through the solid electrolyte layer. Since the internal resistance and gas diffusion coefficient of a solid electrolyte body depend on temperature, it is desirable to precisely control the temperature of the probe in a device according to the invention by means of a heater element such as the illustrated one 63.

Figure 14:
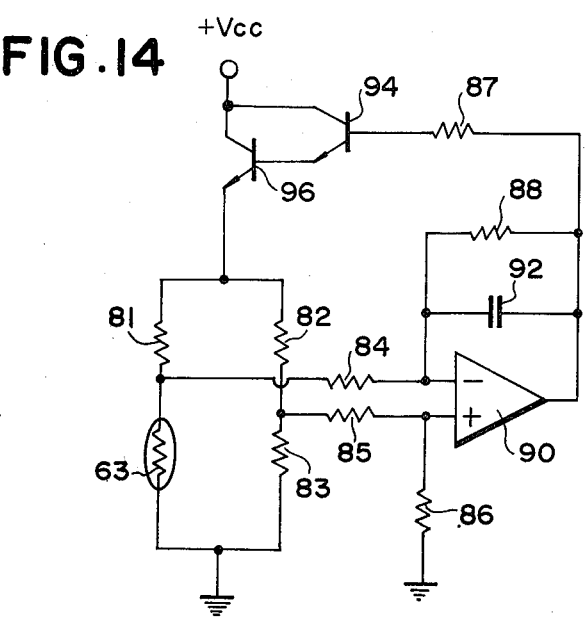
FIG. 14 is a circuit diagram showing an example of a temperature control circuit for application to the device of FIG. 12.

FIG. 14 shows, by way of example, an electrical circuit to accomplish control of the temperature of the probe 60 of FIG. 12. In this circuit, the electrical heating resistance 63 and three resistors 82, 82, 83 constitute a bridge circuit which is connected with an operational amplifier 90 provided with input resistances 84, 85, 86 and a negative feedback circuit including resistance 88 and capacitance 92. Two transistors 94 and 96 are connected to constitute a Darlington circuit, and a source voltage $V_{cc}$ can be supplied to the heating resistance 63 via the transistor 96. The output terminal of the operational amplifier 90 is connected to the base of the transistor 94 via an input resistance 87.

When the temperature of the heating element 63 is below a predetermined level (meaning that the temperature of the substrate 62 or entire probe 60 is below a predetermined level), the resistance of the heater element 63 too becomes smaller than a predetermined value. Then the bridge circuit including the heating resistance 63 becomes unbalanced, resulting in that a higher voltage is applied to the positive input terminal of the operational amplifier 90 than to the negative input terminal. Accordingly the operational amplifier 90 provides an output voltage to the base of the transistor 94 to cause the Darlington circuit to function. As a consequence, the source voltage $V_{cc}$ is applied to the heating resistance 63 via the transistor 96 to continue heating of the substrate 62. When the temperature of the substrate 62 exceeds a predetermined level and the resistance of the heating element 63 becomes too high, the bridge circuit including the resistance 63 becomes unbalanced in such a way that the operational amplifier 90 stops producing the output voltage. Then the Darlington circuit assumes an inoperative state to interrupt the supply of the source voltage $V_{cc}$ to the heating resistance 63. Therefore, the temperature of the substrate 62 begins to lower.

Figure 15:
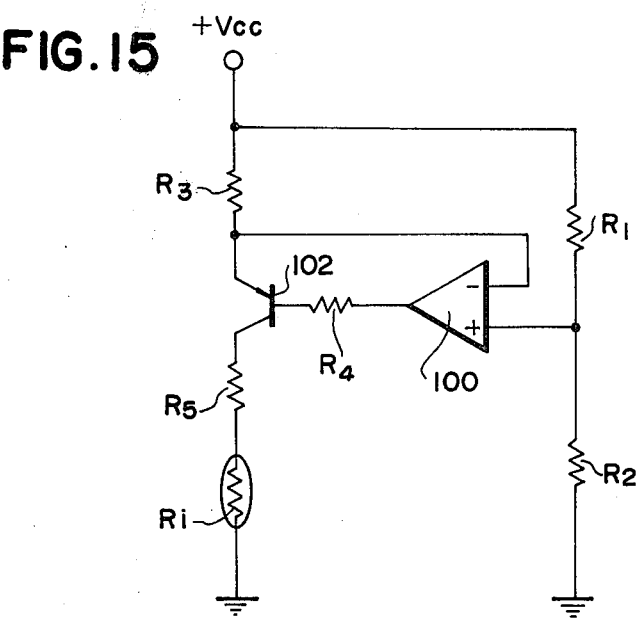
FIG. 15 is a circuit diagram showing an example of a constant current DC power supply circuit for use in a device according to the invention.

FIG. 15 shows an example of a constant current DC power supply circuit preferably used to force a current to flow through the porous solid electrolyte layer 18 in FIG. 1 (or 48 in FIG. 10, or 68 in FIG. 12). In this circuit, two series-connected resistances $R_1$ and $R_2$ constitute a voltage divider to which is applied a source voltage $V_{cc}$. The voltage divider is connected to the positive input terminal of an operational amplifier 100 which provides an output voltage to the base of a transistor 102 via an input resistance $R_4$. Indicated by $R_3$ is an input resistance connected to the emitter of the transistor 102. Indicated by $R_i$ is the internal resistance of the porous solid electrolyte layer 18 (or 48, or 68), which is connected to the collector of the transistor 102 via an output resistance $R_5$.

In this circuit a standard voltage appears across the resistance $R_1$ of the voltage divider, and negative feedback to the operational amplifier 100 causes a voltage drop of the same magnitude as the standard voltage to occur across the resistance $R_3$. An emitter current of the transistor 102 is controlled by the standard voltage, and the controlled emitter current becomes the collector current of the transistor 102, whereby a current I flowing through the solid electrolyte layer or resistance $R_i$ is controlled. The intensity of the current I is given by $$I \div \{R_1/(R_1+R_2)R_3\}V_{cc}$$

This means that a constant current I continues to flow through the solid electrolyte layer 18 (or 48, or 68) even though the internal resistance $R_i$ of this solid electrolyte layer 18 increases or decreases by the influence of temperature.

What is claimed is:

1. A device for detecting the concentration of oxygen in a combustion gas thereby detecting an actual air/fuel ratio of an air-fuel mixture from which the combustion gas was produced, the device comprising a probe to be disposed in the combustion gas, said probe comprising:
   a first electrode which is gas permeable;
   a second electrode spaced from said first electrode;
   an oxygen ion conductive solid electrolyte layer arranged to occupy the space between said first and second electrodes;
   a third electrode which is gas permeably porous and spaced from said second electrode; and
   a gas permeably porous layer of an oxygen ion conductive solid electrolyte arranged to occupy the space between said second and third electrodes;
   at least one of said first and second electrodes being made of a catalytic material which exhibits a catalytic action on oxidation reactions, said first, second and third electrodes being arranged such that the combustion gas directly contacts said first and third electrodes and comes into contact with said second electrode through said gas permeably porous layer occupying the space between said second and third electrodes, so that said probe can generate an electromotive force across said first and second electrodes as an indication of the concentration of oxygen in the combustion gas.

2. A device according to claim 1, further comprising a DC power source connected to said second and third electrodes to force a DC current to flow through said gas permeably porous layer between said second and third electrodes.

3. A device according to claim 2, wherein said DC power source is a constant current DC power supply.

4. A device according to claims 1 or 2, wherein said second electrode is made of said catalytic material, said first electrode being made of a material which does not exhibit a catalytic action on oxidation reactions.

5. A device according to claims 1 or 2, wherein said first and second electrodes are both made of said catalytic material.

6. A device according to claim 1, wherein at least one of said solid electrolyte layer and said gas permeably porous layer is shaped and dimensioned so as to serve as a structurally basic member of said probe.

7. A device according to claim 1, wherein said probe further comprises a substrate which serves as a structurally basic member of said probe, said first, second and third electrodes, said solid electrolyte layer and said gas permeably porous layer each being in the form of a film.

8. A device according to claim 7, wherein said substrate is made of an electrically nonconducting material, said probe further comprising an electrical heater element which is embedded in said substrate.

9. A device according to claim 1, wherein each of said first, second and third electrodes is in the form of a thin layer, said solid electrolyte layer being sandwiched between said first and second electrodes, said gas permeably porous layer covering the outside of said second electrode, said third electrode being formed on the outside of said gas permeably porous layer.

10. A device according to claim 7, wherein each of said first, second and third electrodes is in the form of a thin film, said second electrode being formed on one side of said substrate, said first electrode being formed on said side of said substrate and shaped so as to generally surround said second electrode, said solid electrolyte layer being formed on said side of said substrate so as to fill in the space between said first and second electrodes, said gas permeably porous layer being formed so as to cover the outside of said second electrode and peripherally conjoin said solid electrolyte layer, said third electrode layer being formed on the outside of said gas permeably porous layer.

11. A device according to claim 1, wherein said catalytic material comprises a platinum group metal.

* * * * *